United States Patent [19]

Hecker et al.

[11] 3,986,090

[45] Oct. 12, 1976

[54] MOTOR DRIVE FOR A PART IN AN X-RAY APPARATUS

[75] Inventors: Wolfgang Hecker; Walter Schmedemann, both of Hamburg; Heinrich Hartmann, Reinbek, all of Germany

[73] Assignee: U.S. Philips Corporation, New York, N.Y.

[22] Filed: Dec. 4, 1974

[21] Appl. No.: 529,491

[30] Foreign Application Priority Data

Dec. 13, 1973 Germany.............................. 2361985

[52] U.S. Cl................................. 318/488; 318/17; 318/628; 250/449; 250/525
[51] Int. Cl.²........................................ G05B 11/01
[58] Field of Search ........... 250/522, 523, 525, 401, 250/402; 318/6, 7, 17, 52, 432, 434, 488, 628, 646

[56] References Cited
UNITED STATES PATENTS

| | | |
|---|---|---|
| 2,841,714 | 7/1958 | Vaughn............................. 250/449 |
| 3,215,835 | 11/1965 | Mueller.............................. 250/449 |
| 3,790,805 | 2/1974 | Foderaro ........................... 250/522 |
| 3,866,048 | 2/1975 | Gieschen et al. ................... 250/449 |
| 3,891,856 | 6/1975 | Arnor et al. ........................ 250/525 |

*Primary Examiner*—Robert K. Schaefer
*Assistant Examiner*—John J. Feldhaus
*Attorney, Agent, or Firm*—Frank R. Trifari; Bernard Franzblau

[57] ABSTRACT

The servo drive according to the invention includes a force transducer which is disposed so as to sense all the forces which act on the image-forming section (the weight of the section, the manual force of the user, frictional forces and acceleration forces). On the signal from the transducer there is superposed a signal which corresponds to the weight of said section and to the speed variations $dn/dt$, i.e., to the acceleration forces. Thus the influence of these forces on the output signal is compensated for. The resulting signal serves as the desired value for a speed or acceleration control.

12 Claims, 1 Drawing Figure

U.S. Patent  Oct. 12, 1976  3,986,090
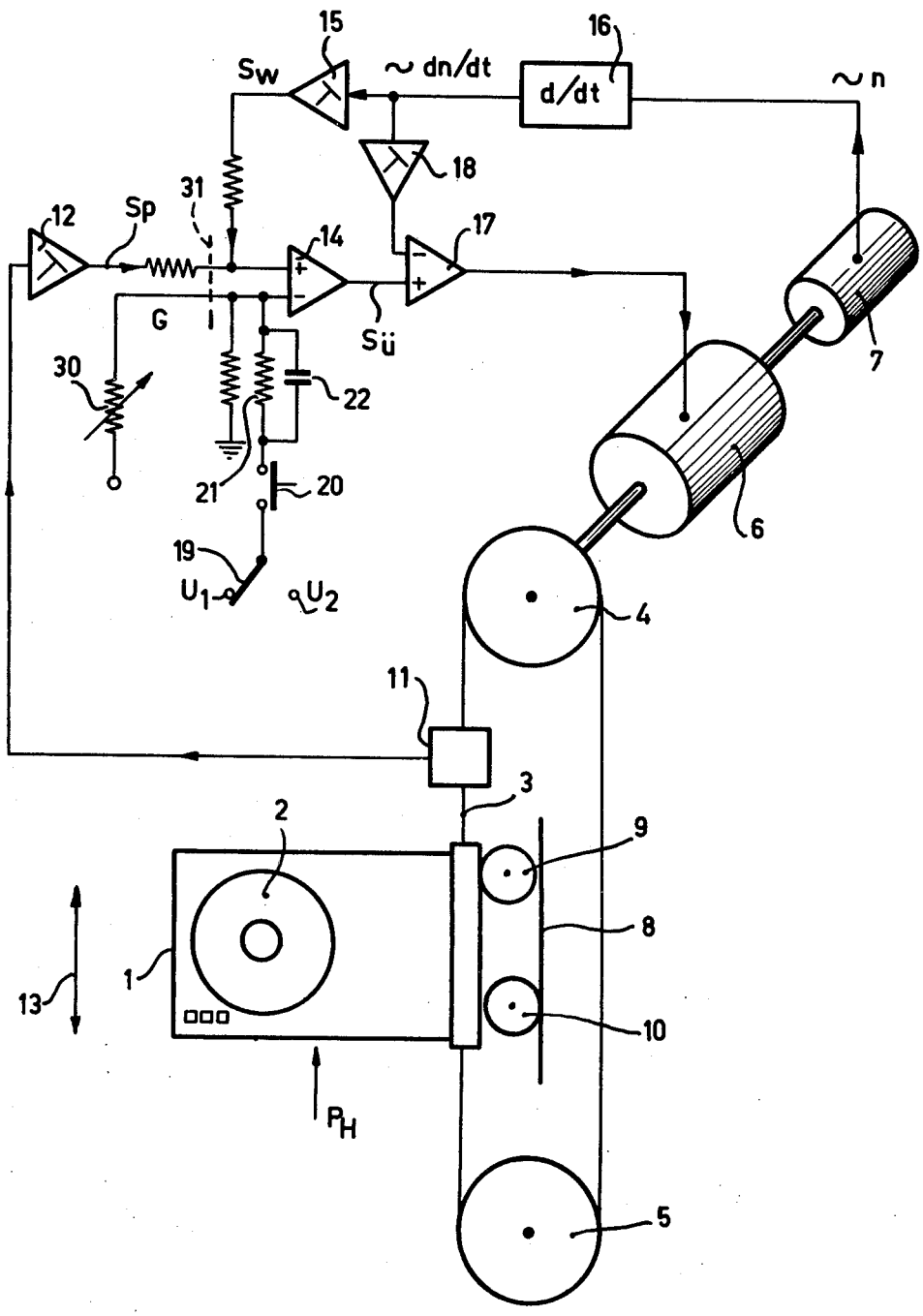

MOTOR DRIVE FOR A PART IN AN X-RAY APPARATUS

The invention relates to a motor drive for displacing a part of an X-ray apparatus provided with a device for controlling the speed and the direction of rotation of the motor, which device includes a force transducer capable of producing a first signal which depends upon the manual force exerted on the part and upon the weight of the part. The device further includes means by which a second signal which corresponds to the said weight of the part can be subtracted from the first signal, the resulting difference signal being used for control purposes.

The introduction of the image intensification technique, of automatic exposure control and the like in radiology has resulted in a progressively increasing weight of the image-forming section owing to the addition of new equipment. Although the weight forces to be overcome can be compensated for by counterweights, the radiologist when moving the image-forming section additionally has to accelerate or decelerate the mass of the counterweight, so that he has to do a large amount of physical work during a working day. Hence various motor drives have been developed to relieve the radiologist of this work.

Motor drives are known in which the speed of the motor and hence the speed at which the image-forming section is displaced (German patent application No. M25099) or the force which the motor exerts on the image-forming section (German Offenlegungsschrift No. 1,566,119) depend upon the force which the user exerts on a handle provided on the said section. The handle is coupled to a transducer which delivers a signal which is used for controlling the speed or the force produced by the motor.

Although such motor drives greatly reduce the work of the radiologist, they do not respond when the image forming section strikes an obstruction, for example a patient. Such a mishap may seriously hurt the patient unless special expensive safety precautions are taken.

Furthermore a motor drive for an X-ray apparatus is known which does not suffer from the said disadvantage and in which the driving energy for the drive motor is controllable by means of the force exerted on the part of the apparatus to be displaced (the image-forming section) (German Gebrauchmuster No. 1,728,886).

This known drive, however, has the disadvantage that the driving energy produced as a function of the force acting on the image-forming section is independent of the fact whether the force acts in the direction of the force of gravity or in the opposite direction. Hence the motional behavior of the image-forming section is different in one diirection from that in the other direction and greatly depends upon the weight of the image-forming section and the particular equipment attached thereto. In the embodiment described, the image-forming section to be displaced is connected to a counterpoise weight by a balance beam so that this beam, which is movable against the force of a spring, is balanced. When a force acts on the image-forming section the beam is moved from its rest position, causing the motor power to be varied as a function of the deviation of the beam from its rest position. However, owing to the springs required to determine the magnitude of the force exerted on the image-forming section, the motor drive may readily be caused to hunt.

A further motor drive for moving a part of an X-ray apparatus is known in which a transducer, more particularly a strain gauge or a quartz crystal, is arranged so as to produce a signal which depends upon the force acting on said part and upon the weight, from which signal a signal which corresponds to the weight is subtracted which serves as the desired value for speed control of the motor (German Auslegeschrift No. 2,104,509). The number of revolutions or speed of the motor and hence the velocity at which it moves the image-forming section as determined by the manual force only. The overall force produced to accelerate the image-forming section and to overcome the frictional forces (motor force + manual force) is smaller than the manual force alone of the user (in the embodiment described part of the motor torque is used to compensate for the weight of the image-forming section). Consequently the user is not really assisted by the servo-motor drive. On the contrary, when displacing the image-forming section, the mass of which in modern X-ray apparatus may be from 200 to 300 kg, he must himself produce the forces required for acceleration and for overcoming the friction.

It is an object of the present invention to provide a motor drive for displacing a section of an X-ray apparatus such that the contribution provided by the motor for overcoming the forces of acceleration and friction can be greater than the force produced by the user, that nevertheless the motor drive responds when the said section strikes an obstruction and that finally when the motor drive is switched or no oscillations occur and the section is moved in the same manner in any direction in accordance with the manual force. For this purpose the motor drive according to the invention is characterized in that means are provided for superposing a further signal on the difference signal, which further signal depends upon motor speed variations, the resulting superposition signal serving as the desired value of an acceleration control or a motor speed control.

This is based on the recognition that during the start of the motor the force exerted by the user on the transducer is partly compensated for by the force exerted by the motor on the said section. The force exerted by the motor on the said section is primarily dependent upon the acceleration and hence upon motor speed variations ($dn/dt$). By superposing the further signal which is dependent upon the mtor speed, (which for example may be measured in known manner by a tacho-generator) the limitation of the motor force inherent in the known apparatus (German Offenlegungsschrift No. 2,104,509) is removed, enabling the motor to exert larger forces on the image-forming section. Thus the further signal must be proportional to the line derivative of the motor speed ($dn/dt$) or, if in a given embodiment of the acceleration control the first signal produced by the transducer or the difference signal is previously integrated, this signal must be proportional to the motor speed $n$.

A further embodiment of the invention is characterized in that in a motor drive in which the superposition signal is used as a desired value for controlling the motor speed, the further signal on the difference signal with a polarity such that the dependence of the difference signal upon the speed variations is at least partly compensated for. When the further signal and the part which is included in the transducer signal and is proportional to the speed variataions have the same amplitude, full compensation is obtained. In the case of acceleration control the aforementioned polarity of the further signal is not absolutely necessary, but it is highly advantageous.

In speed control the acceleration of the image-forming section due to the motor drive is independent of the manual force provided by the user. The acceleration initially is very great, but when the speed has reached the desired value, which corresponds to the manual force, it drops to zero. A disadvantage of speed control is that the radiologist perceives the presence of a motor drive assisting him, which for many persons is undesirable. This disadvantage is absent in acceleration control because in this type of control the force produced by the servo-motor drive is always proportional to the force provided by the radiologist, so that he has the feeling of moving a considerably smaller mass than the actual mass of the section to be moved. Accordingly, in a further embodiment of the invention, the control circuit for acceleration control is such that the actual value for the control circuit can be derived from the output of a differentiating element (which produces a signal proportional to the time derivative of the motor speed $dn/dt$) to the input of which a signal proportional to the measured value of the speed $n$ is applied. The speed signal may be produced, for example, by a tachogenerator.

In a further embodiment of the invention the acceleration control is such that the difference signal or the superposition signal is applied to the input of an integrating element the output of which is connected to the desired-value input of the control circuit, a signal proportional to the measured motor speed being applied to the actual-value input of the control circuit. In this embodiment the control circuit is a speed control circuit. However, a linearly increasing signal is applied to it by the integrating element (when the force measured by the transducer is constant during this time) so that a linearly increasing motor speed and hence constant acceleration are obtained (see U.S. Pat. No. 3,866,048).

An embodiment of the invention will now be described, by way of example, with reference to the accompanying diagrammatic drawing.

Referring now to the single FIGURE, an image-forming section 1, which includes an image intensifier 2, is secured to a chain or rope 3 which passes over pulleys 4 and 5, the pulley 4 being arranged to be driven by a motor 6 to which a tachogenerator 7 is coupled and which produces a signal proportional to the motor speed $n$. The pulleys 4 and 5 are secured to the X-ray apparatus which is not shown except for a guide track 8 for rollers 9 and 10 of the carriage of the image-forming section 1. The part of the chain 3 between the pulley 4, driving the motor 6, and the image-forming section 1, includes a transducer 11 which produces an electric signal which is dependent upon the force acting on the transducer and is applied to the input of a variable-gain amplifier 12. The transducer 11 may, for example, be a strain gauge or a quartz crystal. In principle any transducer may be used which is suitable for measuring a force without being appreciably deformed. Thus oscillation of the motor drive on starting is avoided.

The transducer 11 need not necessarily be located between the driven pulley 4 and the section 1. For the same purpose a strain gauge attached to the shaft of the motor 6 driving the pulley 4 may be used, or a torque transducer which is disposed between the housing of the motor 6 and the X-ray apparatus 8 and which measures the reaction torque. The only important condition is that the transducer is disposed so as to be capable of responding to all the forces which act on the image-forming section in the directions indicated by an arrow 13, i.e., in the directions of displacement. At the output of the amplifier 12 a first signal $s_p$ appears which is proportional to the force exerted on the transducer 11. This signal is applied to the non-inverting input of an operational amplifier 14 to the inverting input of which a signal G is applied which corresponds to the weight of the section 1. The signal G is adjustable by means of a variable resistor 30, so that this weight does not influence the output signal of the operational amplifier 14. A further signal $s_w$ which is proportional to the speed variations $dn/dt$ is also applied to the non-inverting input of the operational amplifier 14. This signal may be derived from a variable gain amplifier 15 the input of which is connected to the output of a differentiating element 16 to the input of which the tachogenerator 7 applies a signal which is proportional to the motor speed $n$ and the polarity of which is changed over in accordance with the direction of rotation by means, not shown. Alternatively a direct-current tachogenerator may be used which provides a signal the polarity of which is dependent upon the direction of rotation.

A superposition signal $s_u$ at the output of the operational amplifier 14 serves as the desired value of an acceleration control. The control circuit for this acceleration control comprises an amplifier 17 of sufficiently high gain the desired-value input of which is connected to the output of the amplifier 14, the motor 6, the tachogenerator 7 and the differentiating element 16 the output of which is connected, via a variable-gain setting element 18, to the other input of the control amplifier 17. The acceleration control circuit operates as follows:

The control amplifier 17 delivers an output signal the amplitude of which depends upon the difference between the desired value $s_u$ (at the output of the operational amplifier 14) and the actual value (at the output of the setting element 18). The control amplifier 17 so controls the motor that its torque is changed in a manner such that the difference between the desired value of the speed variations and the actual value is reduced. Hence when the transducer 11 produces a constant signal and the desired value at the input of the control amplifier 17 is constant, the speed variations $dn/dt$ also will be constant. However, because the speed variations (more properly: the time derivative of the motor speed) are proportional to the acceleration imparted to the section by the motor and hence to the force exerted by the motor 6 on the image-forming section 1, there will be proportionality between the force acting on the transducer 11 and the motor output force.

The differentiating element 16 may be replaced by a setting element the output signal of which is proportional to its input signal if the signal $s_p$ from the amplifier 12, and the signal G which corresponds to the weight of the image-forming section, are supplied to an integrating circuit to be included at the point indicated by a broken line 31. Thus the control circuit comprising the elements 6, 7, 16 and 17 is a true motor-speed control circuit. However, because the desired value of this circuit increases with the time integral of the force exerted on the transducer 11, the motor speed will increase at a rate which is higher as the manual force $P_H$ exerted on the section 1 is greater. This means, however, that the motor speed variation and hence the acceleration force exerted by the motor on the section 1 are proportional to the manual force.

Control circuits which enable the speed or the acceleration of a motor to be controlled are known and hence will not be described in more detail. For a non-synchronous motor such a control loop may have the form described in German Auslegeschrift No. 1,936,915. In a direct-current motor, speed control may, for example, be effected by regulating the armature current in accordance with the output signal of the amplifier 17. Armature current control is advantageous to avoid reactions of the motor voltage on the armature current.

It can be shown that with proper proportioning of the individual control loops the force produced by the motor can be proportional to the manual force produced by the radiologist and may be a multiple thereof. Also the deceleration force produced by the motor drive is a multiple of the deceleration of the image-forming section due to an obstruction. This is the case if the loop amplification in the loop comprising the elements 6, 7, 16, 15, 14 and 17 is positive and exceeds unity and if the loop amplification in the loop comprising the elements 6, 4, 11, 12, 14 and 17 is negative and exceeds the loop amplification of the aforementioned loop (the loop amplification in the loop comprising the elements 6, 7, 16, 18 and 17 obviously must be negative and have a suitable value). With such proportioning the motor drive is stable also. The two control loops comprising the elements 6, 7, 16, 18, 17 and the elements 6, 7, 16, 15, 14, 17 respectively may be combined to form a single control loop if, for example, by means of an attenuator connected to the output of the differentiating element 16 (or to the output of the setting element 15), the amplification via the loop 15, 14 (or via the setting element 18) is taken into account. The element 16 and possibly the element 15 may then be included in the loop which starts from the transducer 11 if the transmission behaviour of this loop, for example by a corresponding variation of the amplifier 12, is adapted so that there is no change in the loop amplification of this loop.

The setting elements or amplifiers 12, 14, 15 and 17 need not necessarily have linear characteristics. It may be desirable to provide lower and upper threshold values so that the motor is not started by a manual force below a given value and does not provide any further acceleration, i.e., does not supply a higher torque, beyond a given manual force.

For moving the image-forming section a given friction has to be overcome. If this friction is excessive or if the manual force (possibly together with the force exerted by the motor) is too small to overcome the friction, the user must increase his manual force. This can be avoided by increasing the desired-value signal, and hence the force exerted by the motor, by an amount such that the frictional forces are just not overcome. The signal to be added for overcoming the friction must have a polarity which depends upon the direction of rotation. It must be larger at the beginning of the displacement of the image-forming section than after the section has commenced moving (after this commencement the signal may even be reduced to zero), because the friction to be overcome in the rest condition is higher than the friction to be overcome during movement of the section.

For this purpose a switch 19 can at will be connected either to a voltage source $U_1$ or to a voltage source $U_2$ of opposite polarity. The switch 19 is controlled by a circuit arrangement, not shown, which provides a signal dependent upon the direction of rotation and which is required for the motor control circuit also. The changeover switch 19 is connected to the input of the operational amplifier 14 via a contact 20 and a resistor 21 shunted by a capacitor 22. The contact 20 is switched into circuit only during displacement (it may for example be controlled in the same manner as brakes, not shown, for locking the image-forming section). The RC section 21, 22 ensures that after closure of the switch 20, i.e., at the beginning of displacement, the signal is very large and then decays to a value determined by the resistance of the resistor 21. The resistor 21 may be dispensed with, in which case the changeover switch 19 is connected to the input of the operational amplifier 14 via the contact 20 and the capacitor 22 only. The signal for overcoming the friction then is operative at the beginning of displacement only.

What is claimed is:

1. A motor drive for displacing a part of an X-ray apparatus comprising, an electric motor coupled to said part, a device for controlling the speed and the direction of rotation of the motor, which device includes a force transducer for producing a first signal which depends upon the manual force exerted on the part and upon the weight of the part, the device further including means for subtracting a second signal which corresponds to said weight of the part from the first signal to derive a resulting difference signal to be used for control purposes, means responsive to the motor for producing a further signal determined by the motor speed variations $dn/dt$, and means for superposing said further signal on the difference signal to derive a resulting superposition signal which serves as the desired value for an acceleration control or for a motor speed control.

2. A motor drive as claimed in claim 1 wherein the superposition signal controls the motor speed, characterized in that the further signal is superposed on the difference signal with a polarity such that the dependence of the difference signal upon motor speed variations is at least partly compensated for.

3. A motor drive as claimed in claim 1 further comprising a control circuit for accelerating the motor and in which the superposition signal is used as the desired value for the control circuit and wherein the means for producing said further signal includes a differentiating element having an input to which a signal proportional to the measured motor speed is applied, the actual value signal for the control circuit being derived from the output of said differentiating element which is coupled to the input of said control circuit.

4. A motor drive as claimed in claim 3 including means for applying the difference signal or the superposition signal to the input of an integrating element the output of which is connected to the desired-value input of the control circuit, a signal proportional to the measured speed ($n$) being applied to the actual-value input of the control circuit.

5. A motor drive as claimed in claim 1 further comprising, means for adding to the superposition signal, at the beginning of displacement, a signal the polarity of which depends upon the direction of motor rotation and which has a value such that it compensates only partly for the influence of the X-ray apparatus part on the superposition signal.

6. A motor drive as claimed in claim 5, characterized in that the signal for compensating the friction is supplied via a contact which is closed only during displacement of said part, and further comprising circuit means being provided which responsive to closure of the contact for providing a short-term increase of the signal.

7. A motor drive system for power assisting an individual in displacing a body free to move comprising, an electric motor coupled to said body for moving same, force transducer means coupled to said body so as to produce a first control signal determined by the manual force exerted on the body and upon the weight of said body, means for deriving a second signal determined by the weight of said body, means for subtractively combining said first and second signals to derive a difference control signal, means responsive to the motor for producing a third signal determined by variations of the motor speed, $dn/dt$, where $n$ is the motor speed and $t$ is time, means for combining said third signal and said difference control signal to derive a fourth control signal that represents the desired signal value for controlling the motor, and circuit means having an input coupled to receive said fourth control signal and an output coupled to the motor for controlling same.

8. A motor drive system as claimed in claim 7 wherein said third signal producing means comprises, means responsive to the motor for generating a voltage proportional to the motor speed, and signal differentiating means responsive to said voltage generating means for deriving said third signal.

9. A motor drive system as claimed in claim 8 wherein said circuit means comprises control amplifier means having a first input coupled to receive said fourth control signal and a second input coupled to the output of the differentiating means to receive said third signal thereby to control the motor in a manner so as to reduce any difference between the values of said third and fourth signals.

10. A motor drive system as claimed in claim 9 wherein said subtractive combining means includes second control amplifier means having a first input coupled to receive said first control signal and a second input coupled to receive said second signal, and wherein the means for combining the third signal and the difference signal comprises means for coupling the third signal to the first input of said second control amplifier means.

11. A motor drive system as claimed in claim 7 further comprising means for compensating the friction and inertia of said body comprising, means for deriving a fifth signal when the body is at rest and is to be displaced, said fifth signal having a polarity which depends upon the direction of motor rotation, and means for modifying said fourth control signal to include said fifth signal.

12. A motor drive system as claimed in claim 11 wherein said compensating means includes an RC circuit coupled to an input of said subtractive combining means for supplying thereto a fifth signal whose amplitude decreases with time.

* * * * *

UNITED STATES PATENT AND TRADEMARK OFFICE
CERTIFICATE OF CORRECTION

PATENT NO. : 3,986,090
DATED : October 12, 1976
INVENTOR(S) : WOLFGANG HECKER ET AL It is certified that error appears in the above-identified patent and that said Letters Patent are hereby corrected as shown below:

Claim 6, line 5, cancel "being provided which";

Signed and Sealed this

Fourteenth Day of December 1976

[SEAL]

Attest:

RUTH C. MASON
*Attesting Officer*

C. MARSHALL DANN
*Commissioner of Patents and Trademarks*